United States Patent
Neto et al.

(10) Patent No.: US 7,462,727 B2
(45) Date of Patent: Dec. 9, 2008

(54) MULTIMETAL OXIDE CONTAINING SILVER, VANADIUM AND A PROMOTER METAL AND USE THEREOF

(75) Inventors: Samuel Neto, Mannheim (DE);
Hartmut Hibst, Schriesheim (DE);
Frank Rosowski, Mannheim (DE);
Sebastian Storck, Mannheim (DE)

(73) Assignee: BASF Aktiengesellschaft (DE)

( * ) Notice: Subject to any disclaimer, the term of this patent is extended or adjusted under 35 U.S.C. 154(b) by 81 days.

(21) Appl. No.: 10/566,019

(22) PCT Filed: Jul. 23, 2004

(86) PCT No.: PCT/EP2004/008296

§ 371 (c)(1),
(2), (4) Date: Jan. 25, 2006

(87) PCT Pub. No.: WO2005/012216

PCT Pub. Date: Feb. 10, 2005

(65) Prior Publication Data

US 2006/0247446 A1    Nov. 2, 2006

(30) Foreign Application Priority Data

Jul. 25, 2003   (DE) .............................. 103 34 132

(51) Int. Cl.
*C07D 307/89* (2006.01)
*C07C 51/255* (2006.01)
*C07C 51/16* (2006.01)
*B01J 23/00* (2006.01)

(52) U.S. Cl. .................. 549/249; 562/412; 502/330; 502/347; 502/353

(58) Field of Classification Search ............ 502/330, 502/347, 353; 549/249; 562/412
See application file for complete search history.

(56) References Cited

U.S. PATENT DOCUMENTS

| | | | |
|---|---|---|---|
| 3,476,118 A | 11/1969 | Luttich | |
| 3,684,741 A | 8/1972 | Friedrichsen et al. | |
| 3,799,886 A | 3/1974 | Felice et al. | |
| 3,871,445 A | 3/1975 | Wanka et al. | |
| 4,137,259 A | 1/1979 | Van Geem et al. | |
| 4,203,906 A | 5/1980 | Takada et al. | |
| 4,256,783 A | 3/1981 | Takada et al. | |
| 4,571,325 A | 2/1986 | Nikolov et al. | |
| 5,225,574 A | 7/1993 | Aichinger et al. | |
| 5,792,719 A | 8/1998 | Eberle et al. | |
| 6,700,000 B1 | 3/2004 | Heidemann et al. | |
| 6,849,574 B1* | 2/2005 | Heidemann et al. | 502/330 |
| 6,919,472 B2* | 7/2005 | Hazin et al. | 558/321 |
| 7,030,054 B2* | 4/2006 | Chigapov et al. | 502/302 |
| 2002/0064497 A1* | 5/2002 | Horne et al. | 423/593 |
| 2006/0235232 A1 | 10/2006 | Neto et al. | |
| 2006/0247446 A1 | 11/2006 | Neto et al. | |
| 2006/0276661 A1 | 12/2006 | Storck et al. | |
| 2007/0060758 A1 | 3/2007 | Storck et al. | |
| 2007/0066836 A1 | 3/2007 | Neto et al. | |

FOREIGN PATENT DOCUMENTS

| | | |
|---|---|---|
| DE | 1 280 756 | 10/1968 |
| DE | 1 769 998 | 2/1972 |
| DE | 1 692 938 | 3/1972 |
| DE | 21 06 796 | 8/1972 |
| DE | 2 201 528 | 11/1972 |
| DE | 28 30 765 | 1/1980 |
| DE | 40 13 051 | 11/1991 |
| DE | 197 05 326 | 8/1998 |
| DE | 198 23 262 A1 | 12/1999 |
| DE | 10334132 A1 | 4/2005 |
| DE | 102005004926 A1 | 8/2006 |
| EP | 0130595 | 1/1985 |
| EP | 0 447 267 | 9/1991 |
| EP | 0 522 871 | 1/1993 |
| EP | 0 744 214 | 11/1996 |
| WO | WO-00/27753 | 5/2000 |
| WO | WO-01/85337 | 11/2001 |
| WO | WO-2004103561 A1 | 12/2004 |
| WO | WO-2004103943 A1 | 12/2004 |
| WO | WO-2004103944 A1 | 12/2004 |
| WO | WO-2005092496 A1 | 10/2005 |

(Continued)

OTHER PUBLICATIONS

Holles et al., "A substrate-versatile catalyst for the selective oxidation of light alkanes. I. Reactivity", *Journal of Catalysis*, vol. 218, pp. 42-53 (2003).

(Continued)

*Primary Examiner*—Cam N. Nguyen
(74) *Attorney, Agent, or Firm*—Connolly Bove Lodge & Hutz LLP

(57) ABSTRACT

A multimetal oxide of the formula I, $$Ag_{a-c}Q_bM_cV_2O_d \cdot e\,H_2O, \qquad I$$

where a is from 0.3 to 1.9, Q is an element selected from among P, As, Sb and/or Bi, is from 0 to 0.3, M is a metal selected from among Nb, Ce, W, Mn, Ta, Pd, Pt, Ru and/or Rh, c is from 0.001 to 0.5, with the proviso that (a-c)≧0.1, d is a number which is determined by the valence and abundance of the elements other than oxygen in the formula I and e is from 0 to 20, and also precatalysts and catalysts produced therefrom for the partial oxidation of aromatic hydrocarbons are described.

18 Claims, No Drawings

FOREIGN PATENT DOCUMENTS

| WO | WO-2005123596 A1 | 10/2005 |
| WO | WO-2006053732 A1 | 5/2006 |
| WO | WO-2006072447 A1 | 7/2006 |

OTHER PUBLICATIONS

Nikolov, V., et al., "Achievements in the production of phthalic anhydride by vapour phase oxide of o-xylene in fixed catalyst bed", Di Sciencza e Techologia, pp. 1-4.

Kershenbaum, L. S., et al., "Dynamic behavior of an industrial scale fixed-bed catalytic reactor", American Chemical Society, 1982, vol. 10, pp. 109-120.

Nikolov, V., et al., Production of phthalic anhydride—status and outlook, Chimija i industrija, 1983, vol. 2, pp. 74-76.

Nikolov, V., et al., "A new approach to the oxidation of o-Xylene into phthalic anhydride in a fixed bed of vanadium-titanium catalyst", Chemical Works, 1988, pp. 157-162.

\* cited by examiner

MULTIMETAL OXIDE CONTAINING SILVER, VANADIUM AND A PROMOTER METAL AND USE THEREOF

RELATED APPLICATIONS

This application is a national stage application (under 35 U.S.C. 371) of PCT/EP2004/00896 filed Jul. 23, 2004 which claims benefit to German application 103 34 132.3 filed Jul. 25, 2003.

The present invention relates to a multimetal oxide comprising silver, vanadium and a promoter metal, its use for producing precatalysts and catalysts for the gas-phase partial oxidation of aromatic hydrocarbons, the (pre)catalysts obtained in this way and a process for preparing aldehydes, carboxylic acids and/or carboxylic anhydrides using the catalysts.

As is known, many anhydrides, carboxylic acids and/or carboxylic anhydrides are prepared industrially by catalytic gas-phase oxidation of aromatic hydrocarbons such as benzene, o-, m- or p-xylene, naphthalene, toluene or durolene (1,2,4,5-tetramethylbenzene) in fixed-bed reactors, preferably shell-and-tube reactors. Depending on the starting material, these oxidations give, for example, benzaldehyde, benzoic acid, maleic anhydride, phthalic anhydride, isophthalic acid, terephthalic acid or pyromellitic anhydride. The oxidations are generally carried out by passing a mixture of a gas comprising molecular oxygen, for example air, and the starting material to be oxidized through a large number of tubes which are arranged in a reactor and each contain a bed of at least one catalyst.

WO 00/27753 and WO 01/85337 describe multimetal oxides comprising silver oxide and vanadium oxide and their use for the partial oxidation of aromatic hydrocarbons.

It is an object of the present invention to improve the yields achieved using these catalysts without having an adverse effect on the selectivities.

We have found that this object is achieved by multimetal oxides of the formula I,

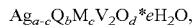

$$Ag_{a-c}Q_bM_cV_2O_d*eH_2O, \quad I$$

where a is from 0.3 to 1.9,

Q is an element selected from among P, As, Sb and Bi, b is from 0 to 0.3,

M is a metal selected from among Nb, Ce, W, Mn, Ta, Pd, Pt, Ru and/or Rh, c is from 0.001 to 0.5, with the proviso that (a-c)≧0.1, d is a number which is determined by the valence and abundance of the elements other than oxygen in the formula I and e is from 0 to 20.

The invention also provides a precatalyst which can be converted into a catalyst for the gas-phase partial oxidation of aromatic hydrocarbons and comprises an inert nonporous support and at least one layer comprising a multimetal oxide as defined above applied thereto.

The invention also provides a catalyst for the gas-phase partial oxidation of aromatic hydrocarbons which comprises an inert nonporous support and, applied thereto, at least one layer comprising, as catalytically active composition, a silver-vanadium oxide bronze which contains at least one metal M selected from the group consisting of Nb, Ce, W, Mn, Ta, Pd, Pt, Ru and/or Rh and in which the Ag:V atomic ratio is from 0.15 to 0.95 and the M:V atomic ratio is from 0.0005 to 0.25, preferably from 0.001 to 0.15.

The invention also provides a process for preparing aldehydes, carboxylic acids and/or carboxylic anhydrides, in which a gaseous stream which comprises an aromatic hydrocarbon and a gas comprising molecular oxygen is brought into contact with a catalyst as defined above at elevated temperature.

The multimetal oxide of the present invention preferably has a crystal structure whose X-ray diffraction pattern displays reflections at lattice plane spacings d of 15.23±0.6, 12.16±0.4, 10.68±0.3, 3.41±0.04, 3.09±0.04, 3.02±0.04, 2.36±0.04 and 1.80±0.04 Å.

In the present patent application, the X-ray reflections are reported in the form of the lattice plane spacings d[Å] which are independent of the wavelength of the X-rays used and can be calculated from the measured diffraction angle by means of the Bragg equation.

In the multimetal oxide of the formula I, the variable a is preferably from 0.5 to 1.0 and particularly preferably from 0.6 to 0.9, the variable b is preferably from 0 to 0.1 and the variable c is preferably from 0.005 to 0.2, in particular from 0.01 to 0.1.

d is determined by the valence and abundance of the elements other than oxygen in the multimetal oxide of the formula I. The number e, which is a measure of the water content, is preferably from 0 to 5.

The specific surface area determined by the BET method and measured in accordance with DIN 66 131, which is based on the "Recommendations 1984" of the International Union of Pure and Applied Chemistry (IUPAC) (cf. Pure & Appl. Chem. 57, 603 (1985)), is generally more than 1 m²/g, preferably from 3 to 250 m²/g, in particular from 10 to 250 m²/g and particularly preferably from 20 to 80 m²/g.

As metals M, preference is given to Nb, Ce, W, Mn and Ta, in particular Ce and Mn, of which Ce is most preferred.

To prepare the multimetal oxides of the invention, it is usual to heat a suspension of vanadium pentoxide ($V_2O_5$) with the solution of a silver compound and a solution of a compound of the metal component M and, if applicable, the solution of a compound of Q. As solvents for this reaction, it is possible to use polar organic solvents such as polyols, polyethers or amines, e.g. pyridine, or preferably water. As silver salt, preference is given to using silver nitrate, but the use of other soluble silver salts, e.g. silver acetate, silver perchlorate or silver fluoride, is likewise possible.

If used, the element or elements Q from the group consisting of P, As, Sb and Bi can be employed in elemental form or as oxides or hydroxides. However, they are preferably used in the form of their soluble compounds, especially their organic or inorganic water-soluble compounds. Among these, particular preference is given to inorganic water-soluble compounds, especially the alkali metal and ammonium salts and in particular the partly neutralized or free acids of these elements, e.g. phosphoric acid, arsenic acid, antimonic acid, ammonium hydrogenphosphates, hydrogenarsenates, hydrogenantimonates and hydrogenbismuthates and alkali metal hydrogenphosphates, hydrogenarsenates, hydrogenantimonates and hydrogenbismuthates. Very particular preference is given to using phosphorus alone as element Q, in particular in the form of phosphoric acid, phosphorous acid, hypophosphorous acid, ammonium phosphate or phosphoric esters and especially as ammonium dihydrogenphosphate.

As salts of the metal component M, it is usual to choose ones which are soluble in the solvent used. If water is used as solvent in the preparation of the multimetal oxides of the present invention, it is possible to use, for example, the perchlorates or carboxylates, in particular the acetates, of the metal component M. Preference is given to using the nitrates of the relevant metal component M, in particular cerium nitrate or manganese nitrate.

The reaction of the $V_2O_5$ with the silver compound, the compound of the metal component M and, if applicable, Q can generally be carried out at room temperature or at elevated temperature. The reaction is generally carried out at from 20 to 375° C., preferably from 20 to 100° C. and particularly preferably from 60 to 100° C. If the temperature of the reaction is above the boiling point of the solvent used, the reaction is advantageously carried out under the autogenous pressure of the reaction system in a pressure vessel. The reaction conditions are preferably chosen so that the reaction can be carried out at atmospheric pressure. The duration of this reaction can be from 10 minutes to 3 days, depending on the type of starting materials reacted and the temperature conditions employed. It is possible to prolong the reaction time of the reaction, for example to 5 days and more. In general, the reaction of the $V_2O_5$ with the silver compound and the compound of the metal component M to form the multimetal oxide of the present invention is carried out over a period of from 6 to 24 hours. The orange-red color of the $V_2O_5$ suspension changes during the reaction and a new compound in the form of a dark brown suspension is formed.

Depending on the desired chemical composition of the multimetal oxide of the formula I, the amounts of $V_2O_5$, silver compound and the compound of the metal component M determined by a and c of formula I are reacted with one another to prepare it. Thus, the silver compound is generally reacted with the vanadium pentoxide in a ratio which corresponds to an atomic ratio of Ag:V of from 0.15 to 0.95, preferably from 0.25 to 0.5, corresponding to a value of a in the formula I of from 0.3 to 1.9 or 0.5 to 1.0, respectively. The silver compound is particularly preferably used in an amount relative to the vanadium pentoxide corresponding to an atomic ratio of Ag:V of from 0.3 to 0.45, corresponding to a value of a in the formula I of from 0.6 to 0.9. The compound of the metal component M is generally used in an amount of from 0.0005 to 0.25, preferably from 0.001 to 0.1, based on $V_2O_5$. After the reaction is complete, the multimetal oxide of the present invention is obtained with a fibrous crystal morphology.

The novel multimetal oxide formed in this way can be isolated from the reaction mixture and stored for further use. The multimetal oxide can be isolated, for example, by filtering the suspension and drying the solid obtained, with drying being able to be carried out both in conventional dryers and also in, for example, freeze dryers. Drying of the multimetal oxide suspension obtained is particularly advantageously carried out by means of spray drying. It can be advantageous to wash the multimetal oxide obtained in the reaction to free it of salts before drying it. Spray drying is generally carried out under atmospheric pressure or reduced pressure. The inlet temperature of the drying gas, generally air, although it is of course also possible to use other drying gases such as nitrogen or argon, is selected according to the pressure employed and the solvent used. The temperature at which the drying gas enters the spray dryer is advantageously chosen so that the outlet temperature of the drying gas which has been cooled by vaporization of the solvent does not exceed 200° C. for any prolonged time. In general, the outlet temperature of the drying gas is set to from 50 to 150° C., preferably from 100 to 140° C. If storage of the multimetal oxide is not intended, the multimetal oxide suspension obtained can also be passed to the further use, for example, the production of the precatalysts of the present invention by coating, without prior isolation and drying of the multimetal oxide.

The multimetal oxides of the present invention are used as precursor compounds for the preparation of the catalytically active composition of catalysts employed for the gas-phase oxidation of aromatic hydrocarbons by means of a gas comprising molecular oxygen to form aldehydes, carboxylic acids and/or carboxylic anhydrides.

Even if the multimetal oxides of the present invention are preferably used for producing coated catalysts, they can also be used as precursor compounds for producing conventional supported catalysts or all-active catalysts, i.e. catalysts which do not contain a support material.

The production of the catalysts of the present invention for the partial oxidation of aromatic hydrocarbons to give aldehydes, carboxylic acids and/or carboxylic anhydrides from the multimetal oxides of the present invention is advantageously carried out via the stage of a "precatalyst" which can be stored and handled as such and from which the active catalyst can be produced either by thermal treatment or in situ in the oxidation reactor under the conditions of the oxidation reaction. The precatalyst is thus a precursor of the catalyst, which comprises an inert nonporous support material and at least one layer applied thereto in the form of a shell, with this layer preferably containing from 30 to 100% by weight, in particular from 50 to 100% by weight, based on the total weight of this layer, of a multimetal oxide of the formula I. The layer particularly preferably consists entirely of a multimetal oxide of the formula I. If the catalytically active layer further comprises additional components in addition to the multimetal oxide of the formula I, these can be, for example, inert materials such as silicon carbide or steatite, or else other known catalysts based on vanadium oxide/anatase for the oxidation of aromatic hydrocarbons to aldehydes, carboxylic acids and/or carboxylic anhydrides. The precatalyst preferably contains from 5 to 25% by weight, based on the total weight of the precatalyst, of multimetal oxide.

As inert nonporous support material for the precatalysts and coated catalysts of the present invention, it is possible to use virtually all support materials of the prior art as are advantageously used in the production of coated catalysts for the oxidation of aromatic hydrocarbons to aldehydes, carboxylic acids and/or carboxylic anhydrides, for example quartz ($SiO_2$), porcelain, magnesium oxide, tin dioxide, silicon carbide, rutile, alumina ($Al_2O_3$), aluminum silicate, steatite (magnesium silicate), zirconium silicate, cerium silicate or mixtures of these support materials. In the present context, the expression "nonporous" should be taken to mean "nonporous except for technically ineffective quantities of pores", since a small number of pores in a support material which should ideally contain no pores can be technically unavoidable. As advantageous support materials, particular mention may be made of steatite and silicon carbide. The shape of the support material is generally not critical for the precatalysts and coated catalysts of the present invention. For example, it is possible to use catalyst supports in the form of spheres, rings, pellets, spirals, tubes, extrudates or granules. The dimensions of these catalyst supports correspond to the catalyst supports customarily used for producing coated catalysts for the gas-phase partial oxidation of aromatic hydrocarbons. As mentioned, the abovementioned support materials can also be mixed in powder form into the catalytically active composition of the coated catalysts of the present invention.

The coating of the inert support material with a shell of the multimetal oxide of the present invention can in principle be carried out using known methods of the prior art. For example, the suspension obtained in the reaction of the vanadium pentoxide with a silver compound, a compound of the metal component M and, if desired, Q can, in accordance with the process of DE-A 16 92 938 and DE-A 17 69 998, be sprayed onto the catalyst supports consisting of an inert support material at elevated temperature in a heated coating drum until the desired amount of multimetal oxide, based on the total weight of the precatalyst, has been reached. In place of coating drums, it is also possible to use, in a manner analogous to DE-A 21 06 796, fluidized-bed coaters as described in DE-A 12 80 756, for applying the multimetal oxide of the present invention in the form of a shell to the catalyst support. In place of the suspension of the multimetal oxide of the present invention as obtained in the reaction, it is also possible to use, particularly preferably, a slurry of the powder of the multimetal oxide of the invention obtained after isolation and drying in these coating processes. As described in EP-A 744 214, organic binders, preferably copolymers, can be added in dissolved form or advantageously in the form of an aqueous dispersion to the suspension of the multimetal oxide of the present invention as is formed in its preparation or a slurry of a powder of the dry multimetal oxide of the present invention in water, an organic solvent such as a higher alcohol, a polyhydric alcohol, e.g. ethylene glycol, 1,4-butanediol or glycerol, dimethylformamide, dimethylacetamide, dimethyl sulfoxide, N-methylpyrrolidone or a cyclic urea, e.g. N,N'-dimethylethyleneurea or N,N'-dimethylpropyleneurea, or in mixtures of these organic solvents with water, with a binder contents of from 10 to 20% by weight, based on the solids content of the suspension or slurry of the multimetal oxide of the present invention, generally being employed. Suitable binders are, for example, vinyl acetate-vinyl laurate, vinyl acetate-acrylate, styrene-acrylate, vinyl acetate-maleate or vinyl acetate-ethylene copolymers. If organic copolymer polyesters, e.g. copolymers based on acrylate-dicarboxylic anhydride-alkanolamine, in a solution in an organic solvent are added to the slurry of the multimetal oxide of the present invention, the binder content can, in a manner analogous to the teachings of DE-A 198 23 262.4, be reduced to from 1 to 10% by weight, based on the solids content of the suspension or slurry.

Coating of the catalyst support with the multimetal oxides of the present invention is generally carried out at coating temperatures of from 20 to 500° C., and can be carried out in the coating apparatus under atmospheric pressure or under reduced pressure. To produce the precatalysts of the present invention, coating is generally carried out at from 0° C. to 200° C., preferably from 20 to 150° C., in particular from room temperature to 100° C. When the catalyst support is coated with a moist suspension of the multimetal oxides of the present invention, it can be advantageous to employ higher coating temperatures, e.g. temperatures of from 200 to 500° C. At the abovementioned lower temperatures, part of a polymeric binder used in the coating process can remain in the layer applied to the catalyst support.

During later conversion of the precatalyst into a coated catalyst according to the present invention by thermal treatment at from >200 to 500° C., the binder is removed from the applied layer by thermal decomposition and/or combustion. The conversion of the precatalyst into a coated catalyst according to the present invention can also be carried out by thermal treatment at above 500° C., for example at temperatures up to 650° C., preferably at from >200 to 500° C., in particular from 300 to 450° C.

Above 200° C., in particular at temperatures above 300° C., the multimetal oxides of the present invention decompose to form catalytically active silver-vanadium oxide bronzes.

For the purposes of the present invention, silver-vanadium oxide bronzes are silver-vanadium oxide compounds having an atomic Ag:V ratio of less than 1. They are generally semi-conducting or metallically conductive, oxidic solids which preferably crystallize in sheet or tunnel structures, with the vanadium in the [$V_2O_5$] host lattice partly being present in reduced form as V(IV).

At appropriately high coating temperatures, part of the multimetal oxides applied to the catalyst support can be decomposed to catalytically active silver-vanadium oxide bronzes and/or silver-vanadium oxide compounds whose crystallographic structure has not been elucidated but which can be converted into the silver-vanadium oxide bronzes mentioned. At coating temperatures of from 300 to 500° C., this decomposition proceeds virtually to completion, so that coating at from 300 to 500° C. gives the coated catalyst of the present invention without going through the precursor stage of the precatalyst.

The coated catalysts of the present invention are preferably produced from the precatalysts of the present invention or are produced in situ from these precatalysts in the reactor for the oxidation of the aromatic hydrocarbons.

During the thermal treatment of the precatalysts of the present invention at from <200 to 650° C., preferably from <250 to 500° C., in particular from 300 to 450° C., the multimetal oxides present in the precatalyst decomposes to form silver-vanadium oxide bronzes. This conversion of the multimetal oxides of the present invention present in the precatalyst into silver-vanadium oxide bronzes also takes place, in particular, in situ in the reactor for the gas-phase partial oxidation of aromatic hydrocarbons to aldehydes, carboxylic acids and/or carboxylic anhydrides, for example in the reactor for preparing phthalic anhydride from o-xylene and/or naphthalene, at the customary temperatures of from 300 to 450° C. when a precatalyst according to the present invention is used in place of the coated catalyst of the present invention in this reaction. In this case, a steady increase in the selectivity of the coated catalyst is generally observed until the conversion of the multimetal oxide of the present invention into the silver-vanadium oxide bronzes is complete. The silver-vanadium oxide bronzes formed in this way are thus a catalytically active constituent of the catalytically active layer of the coated catalyst of the present invention.

The thermal conversion of the multimetal oxides of the present invention into silver-vanadium oxide bronzes proceeds via a series of reduction and oxidation reactions which are not yet understood in detail.

A further possible way of producing a coated catalyst according to the present invention comprises treating the multimetal oxide powder of the present invention thermally at from >200 to 650° C. and coating the inert nonporous catalyst support, if desired with addition of a binder, with the silver-vanadium oxide bronze obtained in this way.

However, the coated catalysts of the present invention are particularly preferably produced from the precatalysts of the present invention in a single stage or, if desired, in a plurality of stages after thermal treatment during or after coating of the catalyst support, in particular in a single stage, in each case in situ in the oxidation reactor under the conditions of the oxidation of aromatic hydrocarbons to aldehydes, carboxylic acids and/or carboxylic anhydrides.

The catalytically active shell of the coated catalyst produced according to the present invention generally contains from 30 to 100% by weight, preferably from 50 to 100% by weight, based on the total weight of the catalytically active shell, of the silver-vanadium oxide bronzes produced in this way, with the silver and the vanadium in the catalytically active shell generally being present in an atomic ratio of Ag:V of from 0.15 to 0.95, preferably from 0.25 to 0.5 and particularly preferably from 0.3 to 0.45. The catalytically active layer of the coated catalysts of the present invention particularly preferably consists entirely of the silver-vanadium oxide bronzes produced according to the present invention. If the catalytically active layer or layers comprises further components in addition to the silver-vanadium oxide bronzes produced according to the present invention, these can be, for example, inert materials according to the prior art, e.g. silicon carbide or steatite, or else catalyst compounds which are not according to the present invention for the oxidation of aromatic hydrocarbons to aldehydes, carboxylic acids and/or carboxylic anhydrides, e.g. catalysts based on vanadium pentoxide/anatase as have been mentioned by way of example in the above discussion of the prior art. The thickness of the catalyst shell comprising the catalytically active constituents is generally from 10 to 250 mm. This also applies when the catalyst shell consists of a plurality of layers applied in succession.

The BET surface area of the coated catalysts of the present invention is generally from 2 to 100 $m^2/g$, preferably from 2 to 40 $m^2/g$ and particularly preferably from 3 to $m^2/g$.

The coated catalysts of the present invention are used for the partial oxidation of aromatic hydrocarbons to aldehydes, carboxylic acids and/or carboxylic anhydrides, in particular for the gas-phase partial oxidation of o-xylene and/or naphthalene to phthalic anhydride or of toluene to benzoic acid and/or benzaldehyde, by means of a gas comprising molecular oxygen. For this purpose, the catalysts of the present invention can be used alone or in combination with other catalysts of differing activity, for example catalysts of the prior art which are based on vanadium oxide/anatase, with the different catalysts generally being located in separate catalyst zones which may be arranged in one or more fixed catalyst beds in the reactor.

The coated catalysts or precatalysts of the present invention are for this purpose introduced into the reaction tubes of a shell-and-tube reactor which are thermostated to the reaction temperature from the outside, e.g. by means of a salt melt. If a precatalyst according to the present invention is used in place of the coated catalyst of the present invention, it is converted into a coated catalyst according to the present invention under the temperature conditions of the partial oxidation of aromatic hydrocarbons to aldehydes, carboxylic acids and/or carboxylic anhydrides, in particular the partial oxidation of o-xylene and/or naphthalene to phthalic anhydride or the partial oxidation of toluene to benzoic acid and benzaldehyde. The reaction gas is passed at from 100 to 650° C., preferably from 250 to 480° C., and a gauge pressure of generally from 0.1 to 2.5 bar, preferably from 0.3 to 1.5 bar, and at a space velocity of generally from 750 to 5000 $h^{-1}$ over the catalyst bed which has been prepared in this way.

The reaction gas supplied to the catalyst is generally produced by mixing a gas which comprises molecular oxygen and may further comprise as suitable reaction moderators and/or diluents such as steam, carbon dioxide and/or nitrogen in addition to oxygen with the aromatic hydrocarbon to the oxidized. The gas comprising molecular oxygen can generally comprise from 1 to 100% by volume, preferably from 2 to 50% by volume and particularly preferably from 10 to 30% by volume, of oxygen, from 0 to 30% by volume, preferably from 0 to 20% by volume, of steam and from 0 to 50% by volume, preferably from 0 to 1% by volume, of carbon dioxide, balance nitrogen. To produce the reaction gas, the gas comprising molecular oxygen is generally loaded with from 30 to 300 g, preferably from 70 to 150 g, of the aromatic hydrocarbon to be oxidized per standard $m^3$ of gas. It is particularly advantageous to use air as gas comprising molecular oxygen.

The gas-phase partial oxidation is advantageously with two or more zones, preferably two zones, of the catalyst bed present in the reaction tube being thermostated to different reaction temperatures, which can be achieved using, for example, reactors having separate salt baths, as are described in DE-A 22 01 528 or DE-A 28 30 765. If the reaction is carried out in two reaction zones as described in DE-A 40 13 051 the reaction zone closest to the inlet for the reaction gas, which generally makes up from 30 to 80% by volume of the total catalyst volume, is generally thermostated to a reaction temperature which is from 1 to 20° C. higher, preferably from 1 to 10° C. higher and in particular from 2 to 8° C. higher, than that in the reaction zone nearest the gas outlet. Such a mode of operation is referred to as two-zone or multizone structuring of the reactor. As an alternative, the gas-phase oxidation can also be carried out at a uniform reaction temperature without division into temperature zones.

In a preferred embodiment of the process for the partial oxidation of aromatic hydrocarbons to aldehydes, carboxylic acids and/or carboxylic anhydrides, which has been found to be particularly advantageous for the preparation of phthalic anhydride from o-xylene and/or naphthalene, the aromatic hydrocarbon is firstly reacted over a bed of the coated catalyst of the present invention to convert it partially into a reaction mixture. The reaction mixture obtained or a fraction thereof can then be brought into contact with at least one further catalyst whose catalytically active composition comprises vanadium pentoxide and anatase.

The gaseous stream is preferably passed successively over a bed of an upstream catalyst and a bed of a downstream catalyst, where the bed of upstream catalyst comprises a catalyst according to the present invention and the bed of downstream catalyst comprises at least one catalyst whose catalytically active composition comprises vanadium pentoxide and anatase. In general, the catalytically active composition of the downstream catalyst comprises from 1 to 40% by weight of vanadium oxide, calculated as $V_2O_5$, from 60 to 99% by weight of titanium dioxide, calculated as $TiO_2$, up to 1% by weight of a cesium compound, calculated as Cs, up to 1% by weight of a phosphorus compound, calculated as P, and up to 10% by weight of antimony oxide, calculated as $Sb_2O_3$. The bed of the downstream catalyst is advantageously made up of at least two layers of catalysts whose catalytically active composition has a differing Cs content, with the Cs content decreasing in the flow direction of the gaseous stream.

In the case of the preparation of phthalic anhydride from o-xylene, the partially reacted reaction mixture comprises, for example, phthalic anhydride and other oxidation products such as o-tolualdehyde, o-toluenecarboxylic acid and phthalide and unreacted o-xylene. It can then be processed further, either by a) separating off the o-xylene from the phthalic anhydride and the other oxidation products which are intermediates on the reaction path from o-xylene to phthalic anhydride and recirculating it and feeding the stream of phthalic anhydride and intermediates into two or more further catalyst beds comprising, for example, a coated catalyst based on vanadium oxide/anatase where the intermediates are selectively oxidized to phthalic anhydride; or by b) passing the product mixture without further work-up, i.e. without o-xylene being separated off, over a second catalyst bed or, if desired, over a further catalyst bed.

This way of carrying out the reaction achieves a significantly higher overall phthalic anhydride yield than when only catalyst systems based on vanadium oxide/anatase are used, since the coated catalysts of the present invention can oxidize o-xylene and/or naphthalene significantly more selectively to phthalic anhydride or the abovementioned intermediates.

The oxidation of toluene to benzaldehyde and/or benzoic acid can be carried out in an analogous fashion. Benzaldehyde is used, for example, as a flavor.

EXAMPLES

A Catalysts

A.1 $Ce_{0.02}Ag_{0.71}V_2O_x$ (Catalyst According to the Present Invention)

102 g of $V_2O_5$ (=0.56 mol) were added whilst stirring to 7 l of deionized water at 60° C. The suspension was admixed with an aqueous solution of 4.94 g of $CeNO_3*6H_2O$ (=0.011 mol, Aldrich, purity 99%). An aqueous solution of 68 g of $AgNO_3$ (=0.398 mol) in 1 l of water was added to the resulting orange suspension while continuing to stir. The temperature of the suspension obtained was subsequently increased to 90° C. over a period of 2 hours and the mixture was stirred for 24 hours at this temperature. The dark brown suspension obtained was then cooled and spray dried (inlet temperature (air)=350° C., outlet temperature (air)=110° C.).

The powder obtained had a specific surface area determined by the BET method of 61 $m^2/g$. An X-ray powder diffraction pattern of the powder obtained was recorded by means of a D 5000 diffractometer from Siemens using Cu—Kα radiation (40 kV, 30 mA). The diffractometer was equipped with an automatic primary and secondary diaphragm system and a secondary monochromator and scintillation detector. The following lattice plane spacings d[Å] with the associated relative intensities $I_{rel}$[%] were observed in the X-ray powder diffraction pattern: 15.04 (11.9), 11.99 (8.5), 10.66 (15.1), 5.05 (12.5), 4.35 (23), 3.85 (16.9), 3.41 (62.6), 3.09 (55.1), 3.02 (100), 2.58 (23.8), 2.48 (27.7), 2.42 (25.1), 2.36 (34.2), 2.04 (26.4), 1.93 (33.2), 1.80 (35.1), 1.55 (37.8).

A.2 $Mn_{0.02}Ag_{0.71}V_2O_x$ (Catalyst According to the Present Invention)

102 g of $V_2O_5$ (=0.56 mol) were added whilst stirring to 7 l of deionized water at 60° C. The suspension was admixed with an aqueous solution of 2.76 g of $Mn(NO_3)_2*4H_2O$ (=0.011 mol, Chempur, purity 98.5%). An aqueous solution of 68 g of $AgNO_3$ (=0.398 mol) in 1 l of water was added to the resulting orange suspension while continuing to stir. The temperature of the suspension obtained was subsequently increased to 90° C. over a period of 2 hours and the mixture was stirred for 24 hours at this temperature. The dark brown suspension obtained was then cooled and spray dried (inlet temperature (air)=350° C., outlet temperature (air)=110° C.).

The powder obtained had a specific surface area determined by the BET method of 58 $m^2/g$. An X-ray powder diffraction pattern of the powder obtained was recorded. The following lattice plane spacings d[Å] with the associated relative intensities $I_{rel}$[%] were observed in the X-ray powder diffraction pattern: 15.09 (6.8), 11.98 (5.7), 10.61 (9.4), 4.36 (16.8), 3.84 (14.7), 3.40 (81.7), 3.09 (61.1), 3.01 (100), 2.58 (26.4), 2.47 (27.9), 2.41 (21.6), 2.36 (37.8), 2.04 (32.2), 1.93 (28.9), 1.80 (42.2), 1.55 (43.4).

A.3 $Ag_{0.73}V_2O_x$ (Comparative Catalyst)

102 g of $V_2O_5$ (=0.56 mol) were added whilst stirring to 7 l of deionized water at 60° C. An aqueous solution of 69.5 g of $AgNO_3$ (=0.409 mol) in 1 l of water was added to the resulting orange suspension while continuing to stir. The temperature of the suspension obtained was subsequently increased to 90° C. over a period of 2 hours and the mixture was stirred for 24 hours at this temperature. The dark brown suspension obtained was then cooled and spray dried (inlet temperature (air)=350° C., outlet temperature (air)=110° C.). The powder obtained had a specific surface area determined by the BET method of 56 $m^2/b$.

For example B.1 below, the powders prepared in this way were applied as follows to magnesium silicate spheres: 300 g of steatite spheres having a diameter of from 3.5 to 4 mm were coated with 40 g of the powder and 4.4 g of oxalic acid with addition of 35.3 g of a mixture of 60% by weight of water and 40% by weight of glycerol at 20° C. in a coating drum over a period of 20 minutes and were subsequently dried. The weight of the catalytically active composition applied in this way, determined on a sample of the precatalyst obtained, was 10% by weight after heat treatment at 400° C. for 1 hour, based on the total weight of the finished catalyst.

For examples B.2 to B.4, the powders were applied as follows to magnesium silicate rings: 350 g of steatite rings having an external diameter of 7 mm, a length of 3 mm and a wall thickness of 1.5 mm were coated with 84.4 g of the powder and 9.4 g of oxalic acid with addition of 66.7 g of a mixture of 60% by weight of water and 40% by weight of glycerol at 20° C. in a coating drum over a period of 20 minutes and were subsequently dried. The weight of the catalytically active composition applied in this way, determined on a sample of the precatalyst obtained, was 18% by weight after heat treatment at 450° C. for 1 hour, based on the total weight of the finished catalyst.

A.4 Reference Catalyst ($V_2O_5/TiO_2$ Two-Layer Catalyst)

1400 g of steatite (magnesium silicate) rings having an external diameter of 8 mm, a length of 6 mm and a wall thickness of 1.6 mm were heated to 160° C. in a coating drum and, together with 13.8 g of an organic binder comprising a copolymer of acrylic acid-maleic acid (weight ratio=75:25), sprayed with a suspension comprising 466 g of anatase having a BET surface area of 21 $m^2/g$, 67.2 g of vanadyl oxalate, 14.4 g of antimony trioxide, 3.15 g of ammonium hydrogenphosphate, 2.87 g of cesium sulfate, 721 g of water and 149 g of formamide. The catalytically active composition applied in this way comprises, on average, 0.16% by weight of phosphorus (calculated as P), 7.5% by weight of vanadium (calculated as $V_2O_5$), 3.2% by weight of antimony (calculated as $Sb_2O_3$), 0.40% by weight of cesium (calculated as Cs) and 88.74% by weight of titanium dioxide.

The coated catalyst obtained in this way was heated to 160° C. in a coating drum and, together with 14 g of an organic binder comprising a copolymer of acrylic acid-maleic acid (weight ratio=75:25), sprayed with a suspension comprising 502 g of anatase having a BET surface area of 21 $m^2/g$, 35.8 g of vanadyl oxalate, 2.87 g of cesium sulfate, 720 g of water and 198 g of formamide. The catalytically active composition applied in this way comprised, on average, 4.0% by weight of vanadium (calculated as $V_2O_5$), 0.4% by weight of cesium (calculated as Cs) and 88.8% by weight of titanium dioxide. The weight of the layers applied was 9.3% by weight of the total weight of the finished catalyst.

A.5 Reference Catalyst ($V_2O_5/TiO_2$ Catalyst)

1400 g of steatite (magnesium silicate) rings having an external diameter of 8 mm, a length of 6 mm and a wall thickness of 1.6 mm were heated to 160° C. in a coating drum and sprayed with a suspension comprising 468 g of anatase having a BET surface area of 21 $m^2/g$, 67.2 g of vanadyl oxalate, 16.8 g of antimony trioxide, 2.95 g of ammonium hydrogenphosphate, 0.72 g of cesium sulfate, 719 g of water and 150 g of formamide until the weight of the layer applied was 10.5% of the total weight of the finished catalyst (after heat treatment at 450° C. for 1 hour). The catalytically active composition applied in this way, i.e. the catalyst shell, comprised, on average, 0.15% by weight of phosphorus (calculated as P), 7.5% by weight of vanadium (calculated as $V_2O_5$), 3.2% by weight of antimony (calculated as $Sb_2O_3$), 0.1% by weight of cesium (calculated as Cs) and 89.05% by weight of titanium dioxide.

B Oxidations

B.1 Preparation of Phthalic Anhydride Using the Catalysts According to the Present Invention from Examples A.1 and A.2 and the Comparative Catalyst from Example A.3

An 80 cm long iron tube having an internal diameter of 16 mm was charged with the catalyst A.1, A.2 or A.3 (coated steatite spheres) to a bed length of 66 cm. To regulate the temperature, the iron tube was surrounded by an electric heating jacket. 360 standard l/h of air laden with 60 g of 98.5% strength by weight o-xylene per standard $m^3$ of air were passed through the tube from the top downward. The results obtained are summarized in the table below.

TABLE

| Catalyst | Stoichiometry of the active composition | Reaction temperature (° C.) | Conversion (%) | $CO_x$—selectivity[1] (%) |
|---|---|---|---|---|
| Catalyst from example A.1 | $Ce_{0.02}Ag_{0.71}V_2O_x$ | 350 | 58 | 11 |
| Catalyst from example A.2 | $Mn_{0.02}Ag_{0.7}V_2O_x$ | 350 | 48 | 13 |
| Comparative catalyst from example A.3 | $Ag_{0.73}V_2O_x$ | 350 | 37 | 10 |

[1] "$CO_x$ selectivity" corresponds to the proportion of the o-xylene which has been converted into combustion products (CO, $CO_2$); the remaining selectivity to 100% corresponds to the proportion of the o-xylene which is converted into the desired product phthalic anhydride and the intermediates o-tolualdehyde, o-toluic acid and phthalide and also by-products such as maleic anhydride, citraconic anhydride and benzoic acid.

A sample of catalyst A.1 removed from the reactor was found to have a BET surface area of the active composition of 6.7 $m^2/g$ and a vanadium oxidation state of 4.63. The following lattice plane spacings d[Å] with the associated relative intensities $I_{rel}$[%] were observed in the X-ray powder diffraction pattern: 4.85 (9.8), 3.50 (14.8), 3.25 (39.9), 2.93 (100), 2.78 (36.2), 2.55 (35.3), 2.43 (18.6), 1.97 (15.2), 1.95 (28.1), 1.86 (16.5), 1.83 (37.5), 1.52 (23.5).

B.2 Preparation of Phthalic Anhydride Using a Combination of the Comparative Catalyst from Example A.3 and the Reference Catalyst A.4 and A.5 in One Tube 0.80 m of the catalyst A.5, 1.40 m of the catalyst A.4 and subsequently 0.80 m of the precatalyst A.3 (coated steatite rings) were introduced from the bottom upward into a 3.85 m long iron tube having an internal diameter of 25 mm. To regulate the temperature, the iron tube was surrounded by a salt melt. 4.0 standard $m^3$/h of air laden with 80 g of 98.5% strength by weight o-xylene per standard $m^3$ of air were passed through the tube from the top downward. At a salt bath temperature of 353-360° C., an average PA yield of 115.5% by weight was achieved (the yield is the amount of phthalic anhydride in percent by weight, based on 100%-pure o-xylene). The conversion was more than 99.94%, and the residue phthalide content at the reactor outlet was less than 0.35% by weight.

B.3 Preparation of Phthalic Anhydride Using a Combination of the Catalysts According to the Invention from Example A.1 and the Reference Catalysts A.4 and A.5 in One Tube The procedure of example B.2 was repeated using 0.80 m of the catalyst A.5, 1.40 m of the catalyst A.4 and subsequently 0.80 m of the precatalyst A.1. An average PA yield of 117.2% by weight was achieved.

B.4 Preparation of Phthalic Anhydride Using a Combination of the Catalysts According to the Present Invention from Example A.2 and the Reference Catalysts A.4 and A.5 in One Tube The procedure of example B.3 was repeated using 0.90 m of the catalyst A.5, 1.60 m of the catalyst A.4 and subsequently 0.50 m of the precatalyst A.1. An average PA yield of 116.7% by weight was achieved. The conversion was more than 99.94%, and the residue phthalide content at the reactor outlet was less than 0.35% by weight. This example shows that when the catalysts of the present invention are used, high PA yields can be achieved even at a bed length of the silver-vanadium oxide catalyst which is significantly shorter than in example B.1.

We claim:

1. A multimetal oxide of the formula I, $$Ag_{a-c}Q_bM_cV_2O_d * e\,H_2O \qquad I$$

where
a is from 0.3 to 1.9,
Q is an element selected from among P, As, Sb and/or Bi,
b is from 0 to 0.3,
M is a metal selected from among Nb, Ce, W, Mn, Ta, Pd, Pt, Ru and Rh,
c is from 0.001 to 0.2, with the proviso that (a-c)≧0.1,
d is a number which is determined by the valence and abundance of the elements other than oxygen in the formula I and
e is from 0 to 20,
which has a crystal structure whose X-ray powder diffraction pattern displays reflections at lattice plane spacings d of 15.23±0.6, 12.16±0.4, 10.68±0.3, 3.41±0.04, 3.09±0.04, 3.02±0.04, 2.36±0.04 and 1.80±0.04 Å.

2. The multimetal oxide according to claim 1, wherein b is 0 and c is from 0.01 to 0.1.

3. The multimetal oxide according to claim 1, which has a specific surface area determined by the BET method of from 3 to 250 $m^2/g$.

4. The multimetal oxide according to claim 1, wherein M is Ce or Mn.

5. A precatalyst, which can be converted into a catalyst for the gas-phase partial oxidation of aromatic hydrocarbons, comprises an inert nonporous support and at least one layer comprising a multimetal oxide according to claim 1 applied thereto.

6. The precatalyst according to claim 5, comprises from 5 to 25% by weight, based on the total weight of the precatalyst, of multimetal oxide.

7. The precatalyst according to claim 5, whose inert nonporous support material comprises steatite.

8. A catalyst for the gas-phase partial oxidation of aromatic hydrocarbons, comprises an inert nonporous support and, applied thereto, at least one layer comprising, as catalytically active composition, a silver-vanadium oxide bronze which comprises at least one metal M selected from the group consisting of Nb, Ce, W, Mn, Ta, Pd, Pt, Ru and Rh, wherein the Ag:V atomic ratio is from 0.15 to 0.95 and the M:V atomic ratio is from 0.0005 to 0.25, which catalyst is produced from a multimetal oxide composition according to claim 1.

9. The catalyst according to claim 8, wherein the silver-vanadium bronze contains Ce or Mn.

10. The catalyst according to claim 8, having a layer whose catalytically active composition has a BET surface area of from 2 to 100 m²/g.

11. A process for preparing aldehydes, carboxylic acids and/or carboxylic anhydrides, comprises bringing a gaseous stream into contact with an aromatic hydrocarbon and a gas comprising molecular oxygen in the presence of a catalyst according to claim 8 at elevated temperature.

12. The process according to claim 11, wherein the catalyst is produced in situ from a precatalyst which can be converted into a catalyst, the catalyst comprises an inert nonporous support and at least one layer comprising a multimetal oxide of the formula I, $$Ag_{a-c}Q_bM_cV_2O_d*e\ H_2O \qquad I$$

where
a is from 0.3 to 1.9,
Q is an element selected from among P, As, Sb and/or Bi,
b is from 0 to 0.3,
M is a metal selected from among Nb, Ce, W, Mn, Ta, Pd, Pt, Ru and Rh,
c is from 0.001 to 0.2, with the proviso that (a-c)>0.1,
d is a number which is determined by the valence and abundance of the elements other than oxygen in the formula I and
e is from 0 to 20,
which has a crystal structure whose X-ray powder diffraction pattern displays reflections at lattice plane spacings d of 15.23+0.6, 12.16+0.4, 10.68+0.3, 3.41+0.04, 3.09+0.04, 3.02+0.04, 2.36+0.04 and 1.80+0.04 Å.

13. The process according to claim 11, wherein the reaction mixture obtained or a fraction thereof is brought into contact with at least one further catalyst whose catalytically active composition comprises vanadium pentoxide and anatase, wherein said anatase is a form of titanium dioxide.

14. The process according to claim 13, wherein the gaseous stream is passed successively over a bed of an upstream catalyst and a bed of a downstream catalyst, wherein the bed of upstream catalyst comprises a catalyst comprises an inert nonporous support and, applied thereto, at least one layer comprising, as catalytically active composition, a silver-vanadium oxide bronze which comprises at least one metal M selected from the group consisting of Nb, Ce, W, Mn, Ta, Pd, Pt, Ru and Rh, wherein the Ag:V atomic ratio is from 0.15 to 0.95 and the M:V atomic ratio is from 0.0005 to 0.25, which catalyst is produced from said multimetal oxide of formula (I) and the bed of downstream catalyst comprises at least one catalyst whose catalytically active composition comprises vanadium pentoxide and anatase.

15. The process according to claim 14, wherein the catalytically active composition of the downstream catalyst comprises from 1 to 40% by weight of vanadium oxide, calculated as $V_2O_5$, from 60 to 99% by weight of titanium dioxide, calculated as $TiO_2$, up to 1% by weight of a cesium compound, calculated as Cs, up to 1% by weight of a phosphorus compound, calculated as P, and up to 10% by weight or antimony oxide, calculated as $Sb_2O_3$.

16. The process according to claim 15, wherein the bed of the downstream catalyst comprises at least two layers of catalysts whose catalytically active composition has a differing Cs content, with the Cs content decreasing in the flow direction of the gaseous stream.

17. The process according to claim 11, wherein o-xylene or naphthalene or a mixture of o-xylene and naphthalene is used as aromatic hydrocarbon and is oxidized to phthalic anhydride.

18. The process according to claim 11, wherein the reaction mixture obtained or a fraction thereof is brought into contact with at least one further catalyst whose catalytically active composition comprises vanadium pentoxide and anatase, wherein said anatase is a form of titanium dioxide.

* * * * *